US010155786B2

(12) United States Patent
Myerson et al.

(10) Patent No.: US 10,155,786 B2
(45) Date of Patent: Dec. 18, 2018

(54) PRESSURE DRIVEN FLOW CRYSTALLIZER

(71) Applicant: Massachusetts Institute of Technology, Cambridge, MA (US)

(72) Inventors: Allan S. Myerson, Boston, MA (US); Marcus O'Mahony, Cambridge, MA (US); Torsten Stelzer, San Juan, PR (US); Yuqing Cui, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/530,181

(22) Filed: Dec. 8, 2016

(65) Prior Publication Data

US 2017/0166601 A1 Jun. 15, 2017

Related U.S. Application Data

(60) Provisional application No. 62/264,843, filed on Dec. 8, 2015.

(51) Int. Cl.
*B01J 19/00* (2006.01)
*C07H 17/08* (2006.01)
*B01D 9/00* (2006.01)
*C07C 213/10* (2006.01)

(52) U.S. Cl.
CPC .......... *C07H 17/08* (2013.01); *B01D 9/0004* (2013.01); *B01D 9/0013* (2013.01); *B01D 9/0031* (2013.01); *B01D 9/0036* (2013.01); *B01D 9/0054* (2013.01); *C07C 213/10* (2013.01); *C07B 2200/13* (2013.01)

(58) Field of Classification Search
CPC ...... B01J 19/00; B01J 19/0006; B01J 19/004; B01J 19/0053; B01J 2219/00279
See application file for complete search history.

(56) References Cited

U.S. PATENT DOCUMENTS

| 4,144,308 | A | 3/1979 | Johnson |
| 4,865,992 | A | 9/1989 | Hach et al. |
| 5,264,315 | A | 11/1993 | Tan et al. |
| 2009/0214585 | A1 | 8/2009 | Ciocca et al. |
| 2011/0021749 | A1 | 1/2011 | Demmitt |
| 2016/0279246 | A1 | 9/2016 | Trout et al. |

FOREIGN PATENT DOCUMENTS

| WO | WO 2009/023515 A2 | 2/2009 |
| WO | WO 2016/025803 A1 | 2/2016 |

OTHER PUBLICATIONS

Invitation to Pay Additional Fees for PCT/US2016/000122 dated Jan. 25, 2017.

(Continued)

*Primary Examiner* — Robert M Kunemund
(74) *Attorney, Agent, or Firm* — Wolf, Greenfield & Sacks, P.C.

(57) ABSTRACT

The present invention generally relates to systems and methods for pressure driven flow crystallization. In some embodiments, the system comprises a comprising a cavity and a mixing mechanism. In some embodiments, one or more inlets facilitate the transfer of one or more reagent streams to the cavity. In some such embodiments, the mixing mechanism mixes the first and second reagent streams such that a continuous crystallization and/or generation of a product (e.g., solid particles) in the fluid.

18 Claims, 9 Drawing Sheets

(56) References Cited

OTHER PUBLICATIONS

International Search Report and Written Opinion for PCT/US2016/000122 dated Apr. 13, 2017.

Alvarez et al., Crystallization of cyclosporine in a multistage continuous MSMPR crystallizer. Crystal Growth & Design. Aug. 31, 2011;11(10):4392-400.

Bennett et al., Crystallizer influenced nucleation. Chem Eng Prog. 1973;69:86-93.

Cui et al., Custom-Built Miniature Continuous Crystallization System with Pressure-Driven Suspension Transfer. Org Process Res Dev. 2016;20(7):1276-82.

Hartman, Managing solids in microreactors for the upstream continuous processing of fine chemicals. Organic Process Research & Development. Apr. 16, 2012;16(5):870-87.

Hou et al., Development and Characterization of a Single Stage Mixed-Suspension, Mixed-Product-Removal Crystallization Process with a Novel Transfer Unit. Cryst Growth Des. 2014;14(4):1782-93.

Johnson et al., Development and Scale-Up of a Continuous, High-Pressure, Asymmetric Hydrogenation Reaction, Workup, and Isolation. Org Process Res Dev. 2012;16(5):1017-38.

Kougoulos et al., Estimation of crystallization kinetics for an organic fine chemical using a modified continuous cooling mixed suspension mixed product removal (MSMPR) crystallizer. Journal of Crystal Growth. Jan. 2005;273(3-4):520-8.

Ma et al., New developments in particle characterization by laser diffraction: size and shape. Powder Technology. Aug. 2000;111(1-2):66-78.

Moschou et al., Advances in continuous crystallization: toward microfluidic systems. Reviews in Chemical Engineering; Apr. 2014;30(2):127-38.

Nishio et al., A small-scale continuous mixed suspension mixed product removal crystallizer. Chem Eng Sci. 1991;46(2):709-11.

Nyvlt et al., Crystallization using recycle of mother liquor. Int. Chem. Eng. 1979;19:547-52.

Palacio et al., Solid-state characterization of two polymorphic forms of R-albuterol sulfate. Journal of pharmaceutical and biomedical analysis. Mar. 12, 2007;43(4):1531-4.

Polster et al., Pilot-Scale Continuous Production of LY2886721: Amide Formation and Reactive Crystallization. Org Process Res Dev. 2014;18(11):1295-309.

Shiau et al., Model for a cascade crystallizer in the presence of growth rate dispersion. Ind Eng Chem Res. 1987;26(12):2515-21.

Tavare et al., Crystal Size Distribution From a Cascade of Msmpr Crystallizers With Magma Recycle. Chem Engineering Comm; 1986;47(4-6): 185-99.

Teoh et al., Practical Assessment Methodology for Converting Fine Chemicals Processes from Batch to Continuous. Org Process Res Dev. 2016;20(2):414-31.

White et al., Optimum fines size for classification in double draw-off crystallizers. Ind Eng Chem Res. 1989;28(3):276-84.

Zubata et al., A new HPLC method for azithromycin quantitation. Journal of pharmaceutical and biomedical analysis. Feb. 1, 2002;27(5):833-6.

Components:
A - dip tube outlet
B - feed tube
C - air-in tube
D - stir shaft
E - magnetic impeller
F - jacket cavity
G - Magnetic stir plate

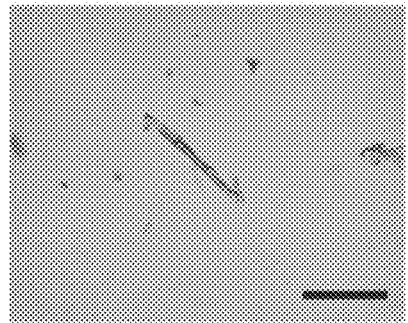
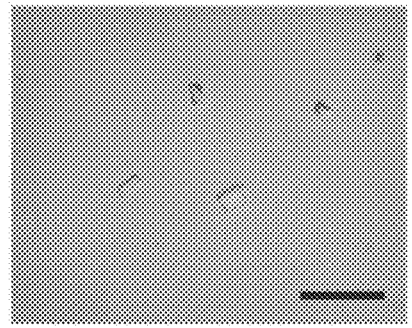
FIG. 11A   FIG. 11B
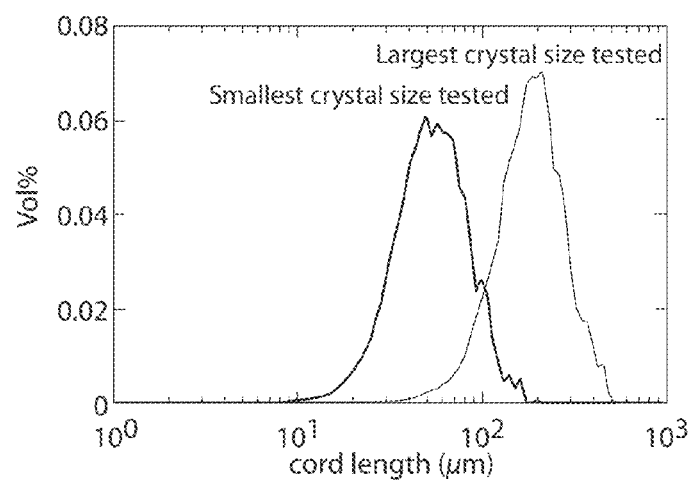
FIG. 12

PRESSURE DRIVEN FLOW CRYSTALLIZER

RELATED APPLICATIONS

This application claims priority under 35 U.S.C. § 119(e) to U.S. Provisional Application Ser. No. 62/264,843, filed Dec. 8, 2015, which is incorporated herein by reference in its entirety for all purposes.

STATEMENT REGARDING FEDERALLY SPONSORED RESEARCH

This invention was made with Government support under Contract No. N66001-11-C-4147 awarded by the Space and Naval Warfare Systems Center. The Government has certain rights in the invention.

FIELD OF THE INVENTION

The present invention generally relates to systems and methods for pressure driven flow crystallization.

BACKGROUND

The pumping and transfer of solids and slurries has generally primarily been of concern only for large scale industrial applications (e.g. liters per min in the transfer of sand and oil slurries in the petrochemical sector or the transfer of coal slurries). These types of slurries are readily handled by centrifugal pumps with large internal clearances.[1] Process intensification and continuous flow processing in the pharmaceuticals and fine chemicals industry often requires the use of small scale channels and microreactors (e.g., having a volume on the order of milliliters or microliters) or small continuously operated vessels such as Continuous Stirred Tank Reactors (CSTRs). Operations at these scales, where solid-liquid mixtures are required to flow, the risk of plugging or clogging is ever present. Accordingly, improved systems and methods are needed.

SUMMARY OF THE INVENTION

The present invention provides systems and methods for pressure driven flow crystallization.

In one aspect, methods are provided. In some embodiments, the method comprises providing a reaction vessel including at least one inlet for introduction of a reactant, and at least one outlet for recovery of a product, wherein the outlet is constructed and arranged such that it facilitates removal of the product when a volume of substance in the vessel is at least a threshold volume, but not to facilitate removal of the product when a volume of substance in the vessel is below the threshold volume, and controlling pressure internally of the vessel so as to remove a given volume of the product from the vessel when the volume of substance in the vessel is at least at the threshold volume, while not removing a volume of the product from the vessel when the volume of substance in the vessel is below the threshold volume.

In some embodiments, the method comprises providing to a cavity of a reaction vessel, through a first inlet fluidically connected to the cavity, a first fluid, providing to the cavity of the reaction vessel, through a second inlet fluidically connected to the cavity, a second fluid, mixing the first fluid and the second fluid to form a product, measuring the volume of the product in the cavity, and upon reaching a critical vertical volume of the product, applying a pressure to the cavity such that at least a portion of the product flows through a vertically oriented outlet fluidically connected with the cavity to a receiving vessel, wherein the cavity has a volume of less than 1 L and/or wherein a flow rate of the fluid through the vertically oriented outlet is greater than a sedimentation rate of the product in the fluid.

In some embodiments, the method comprises providing to a cavity of a reaction vessel, through a first inlet fluidically connected to the cavity, a first fluid, providing to the cavity of the mixing vessel, through a second inlet fluidically connected to the cavity, a second fluid, mixing the first fluid and the second fluid to form a product, and periodically applying a pressure to the cavity such that at least a portion of the product flows through a vertically oriented outlet fluidically connected with the cavity to a receiving vessel, wherein the cavity has a volume of less than 1 L and/or wherein a flow rate of the fluid through the vertically oriented outlet is greater than a sedimentation rate of the product in the fluid.

In another aspect, systems are provided. In some embodiments, the system comprises a vessel comprising a mixing mechanism and a cavity, a first inlet fluidically connected to the cavity, a second inlet fluidically connected to the cavity, a vertically oriented outlet fluidicially connected to the cavity, and a pump, configured to apply a pressure to the cavity periodically, wherein the volume of the cavity is less than 1 L.

In some embodiments, the system comprises a vessel comprising a mixing mechanism and a cavity, a first inlet fluidically connected to the cavity, a second inlet fluidically connected to the cavity, a vertically oriented outlet fluidicially connected to the cavity, a fluid height sensor, and a pump, configured to apply a pressure to the cavity upon a fluid internal to the cavity reaches a critical fluid height, wherein the volume of the cavity is less than 1 L.

In some embodiments, the system comprises a reaction vessel including at least one inlet for introduction of a reactant, and at least one outlet for recovery of a product, a sensor constructed to determine volume of the product in the vessel, and a conduit in fluid communication with the vessel, and a valve associated with the conduit switchable from a position releasing pressure from the vessel above a threshold pressure, and to apply pressure internally of the vessel upon a signal indicative of a threshold volume of the product in the vessel.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

FIGS. 11A-11B are exemplary photographs of crystal shapes transferred by the system including (A) albuterol needle crystals and (B) azithromycin rectangular-shaped crystals. Scale bar represents 50 microns; and FIG. 12 is a plot of crystal size distribution of the smallest and the largest crystal sizes tested, according to some embodiments.

Figure 1:
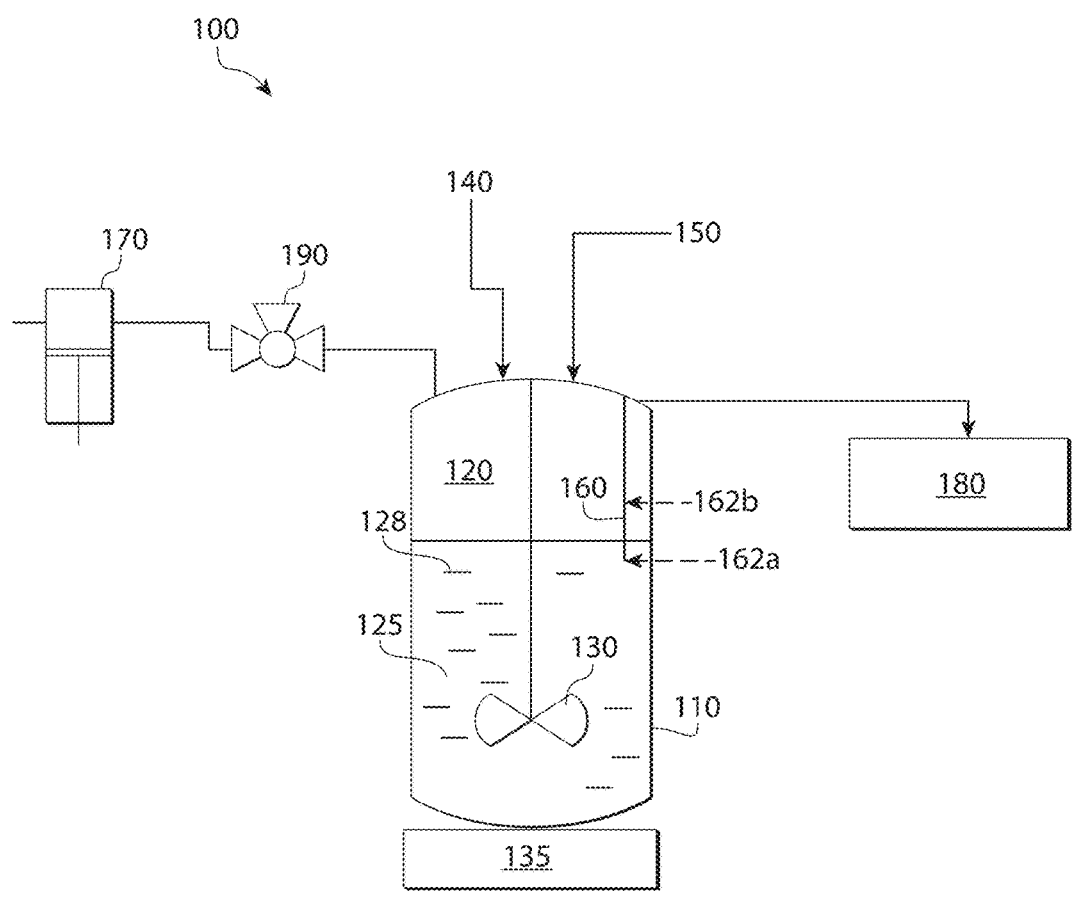
FIG. 1 is a schematic illustration of a system for pressure driven flow crystallization, according to some embodiments.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to systems and methods for pressure driven flow crystallization.

The ability to manufacture chemical products (e.g., active pharmaceutical ingredients (APIs)) in a portable, self-contained, and/or readily reconfigurable chemical process remains generally elusive. For example, chemical synthesis, purification, formulation, and final packaging steps typically require large-scale facilities and expensive operations. These facilities generally require long timescales to develop manufacturing methods and to proceed from synthesizing of chemical products and ingredients to the release of a finished chemical (e.g., pharmaceutical) product. Furthermore, manufacturing delays and shortages can often result when large batches of chemical products fail quality control testing. Additionally, the facilities used to manufacture chemical products are typically designed for the manufacturing of one particular chemical product, and generally require extensive disassembly and reassembly in order to manufacture additional chemical products. Certain of the systems and methods described herein can provide one or more advantages over traditional chemical (e.g., pharmaceutical) manufacturing systems and methods.

Some embodiments described herein may be used in a variety of applications that can benefit from the ability to synthesize chemical products in a continuous process. For example, a large percentage of active pharmaceutical ingredients are typically formulated in discrete batch or semi-batch processes. The ability to synthesize active pharmaceutical ingredients in a continuous manner can allow for a significant reduction in footprints of required facilities, as well as the development of novel synthesis methods.

In some embodiments, the systems and methods described herein may be used in applications requiring the transfer and pumping of solid contained in liquid phases. For example, the systems may be utilized in R&D laboratory scale processing or novel desktop scale processing and could be adapted to facilitate the processing of larger volumes (e.g., volume flow rates) for continuous manufacture in industries such as pharmaceuticals, foods, polymers, dyes, explosives, and others. In some cases, the systems and methods described herein may be useful in areas of chemical synthesis that involve crystallization or solids precipitation or the use of solid catalysts or functionalized supports for reaction.

Advantageously, the systems and methods described may facilitate the pumping and/or transfer of fluids containing suspended solid particles. In some embodiments, the fluid may be transferred at a relatively low volumetric flow rate (e.g., less than 10 milliliters per minute). The systems and methods described herein may be useful in chemical processing of fine chemical or active pharmaceutical ingredients in, for example, flow synthesis processes and/or continuous crystallization of solids from a solution. The systems described herein may be used, for example, for cooling and antisovlent crystallization, with one or more solvents, with products comprising crystals having large aspect ratios and/or size ranges.

In certain embodiments, a vessel (e.g., a reaction vessel) comprises a cavity having a relatively low volume (e.g., less than 1 L). Current methods to transfer slurries between vessels on the laboratory scale generally operate, for example, positive displacement pumps. For example, peristaltic pumps generally operate with very low suspension densities and may be prone to clogging. Similarly, diaphragm pumps typically have small suction cavities that can become easily blocked. Advantageously, the systems and methods described herein may, in some embodiments, convey slurries (e.g., suspended solid solutions) at relatively low volume flow rates (e.g., nanoliter per min to microliter per minute) and/or volumes (e.g., less than 1 L) as compared to traditional pressure driven systems, without clogging or blocking.

In some embodiments, the system comprises a vessel (e.g., a reaction vessel) comprising a cavity and a mixing mechanism. In some embodiments, the system comprises a comprising a cavity and a mixing mechanism. In some embodiments, one or more inlets facilitate the transfer of one or more reagent streams to the cavity. In some such embodiments, the mixing mechanism mixes the first and second reagent streams such that a continuous crystallization and/or generation of a product (e.g., solid particles) in the fluid.

Referring now to FIG. 1, system 100 comprises vessel 110. In some embodiments, vessel 110 comprises cavity 120 and mixing mechanism 130. In certain embodiments, the system comprises one or more inlets fluidically connected to the cavity. For example, in some embodiments, system 100 comprises first inlet 140 fluidically connected to cavity 120 and second inlet 150 fluidically connected to cavity 120. In some embodiments, the first inlet facilitates the transfer of a first reagent stream to the cavity and the second inlet facilitates the transfer of a second reagent stream to the cavity. In some such embodiments, the mixing mechanism mixes the first and second reagent streams such that a continuous crystallization and/or generation of a product (e.g., solid particles) in fluid 125, contained within cavity 120 of vessel 110. For example, in certain embodiments, two or more reagent streams are added to the cavity such that a product (e.g., plurality of solid particles 128) is generated and/or crystallized in a fluid from a liquid phase of the fluid.

In some embodiments, the cavity has a particular volume. In certain embodiments, the volume of the cavity is less than or equal to 1 L, less than or equal to 500 mL, less than or equal to 250 mL, less than or equal to 200 mL, less than or equal to 100 mL, less than or equal to 50 mL, less than or equal to 40 mL, or less than or equal to 25 mL. In some embodiments, the volume of the cavity is greater than or equal to 20 mL, greater than or equal to 25 mL, greater than or equal to 40 mL, greater than or equal to 50 mL, greater than or equal to 100 mL, greater than or equal to 200 mL, greater than or equal to 250 mL, or greater than or equal to 500 mL. Combinations of the above-referenced ranges are also possible (e.g., less than or equal to 1 L and greater than or equal to 25 mL, less than or equal to 200 mL and greater than or equal to 40 mL). Other ranges are also possible.

In some embodiments, the mixing mechanism maintains the suspension of the product (e.g., plurality of solid particles) within the fluid in the cavity. In some embodiments, the mixing mechanism comprises an axial flow impeller. The fluid can be mixed using static mixers, in some embodiments. In some embodiments, the mixing mechanism comprises a stir bar, an impeller, or the like to facilitate mixing of the first reagent and the second reagent. In some embodiments, the mixing mechanism comprises a micromixer and/or an embedded static macromixer. The mixing mechanism may be constructed from any suitable material (e.g., PEEK, PTFE, ETFE, stainless-steel, glass or any other suitable materials). Other mixing mechanisms are also possible and those skilled in the art would be capable of selecting mixing mechanisms based upon the teachings of this specification. The axial flow impeller or other mixing mechanism may be magnetic, such that an external magnet may facilitate the rotation of the mixing mechanism. For example, as shown in FIG. 1, magnet stage 135 may facilitate the rotation of mixing mechanism 130.

Referring again to FIG. 1, in some embodiments, system 100 comprises vertically oriented outlet 160 fluidically connected to the cavity. In some embodiments, the pressure internal of the vessel may be controlled. In certain embodiments, a pump may be fluidically connected to and configured to apply a pressure internal of the vessel to the cavity. For example, in some embodiments, pump 170 may be fluidically connected and configured to apply a pressure to cavity 120 such that at least a portion of fluid 125 (e.g., comprising plurality of solid particles 128) enters vertically oriented outlet 160 and is transferred out of vessel 120.

Advantageously, the use of a vertically oriented outlet generally prevents product or the fluid present in the cavity from settling into the outlet and/or eliminates the need for additional valve(s) on the outlet to control fluid flow through the outlet, as compared to traditional chemical (e.g., pharmaceutical) manufacturing systems and methods. In some embodiments, the vertically oriented outlet comprises a dip tube.

In some embodiments, the pump is configured to apply a pressure to cavity 120 when fluid 125 reaches a threshold height (or threshold volume). For example, in some embodiments, fluid 125 has at least a first height 162*a* where pump 170 is configured not to apply a pressure to cavity 120, and at least a second height 162*b* (i.e. the threshold height) where pump 170 is configured to apply a pressure to fluid 125 internal of cavity 120 such that fluid 125 enters vertically oriented outlet 160 and exits the vessel. In some embodiments, pump 170 comprises a solenoid dosing pump.

In some embodiments, a flow rate of the fluid (e.g., comprising the product) through the vertically oriented outlet is greater than a sedimentation rate of the product in the fluid. For example, in some embodiments, a pressure is applied by the pump to the fluid internal of the cavity such that the fluid comprising the product passes through the vertically oriented outlet at a flow rate greater than the sedimentation rate of the product in the fluid, in the absence of flow.

In some embodiments, the system comprises a sensor (e.g., comprising a fluid height sensor, comprising a timer) constructed to determine volume of the product in the vessel and that signals the pump to apply (e.g., at or above a threshold volume) or not apply (e.g., below the threshold volume) a pressure to the fluid internal of the vessel. In some embodiments, the methods comprise providing a vessel including at least one inlet for introduction of a reactant, and at least one outlet for recovery of a product, wherein the outlet is constructed and arranged such that it facilitates removal of the product when a volume of substance in the vessel is at least a threshold volume, but not to facilitate removal of the product when a volume of substance in the vessel is below the threshold volume.

In some such embodiments, the pressure internal of the vessel may be controlled so as to remove a given volume of the product (e.g., the plurality of suspended solids) from the vessel when the volume of substance in the vessel is at least at the threshold volume, while not removing a volume of the product from the vessel when the volume of substance in the vessel is below the threshold volume. In certain embodiments, the pressure internal of the vessel may be controlled to release, from the vessel, pressure above a threshold pressure when the volume of substance in the vessel is below the threshold volume.

For example, in an exemplary embodiment, fluid 125 is at first height 162*a*, as determined by the sensor, and pump 170 does not apply a pressure to cavity 120. A first reagent may be added to first inlet 140 and a second reagent may be added to second inlet 150 such that fluid 125 increases in volume such that the sensor determines that fluid 125 is at second height 162*b*. Once reaching second height 162*b*, the sensor may signal pump 170 such that fluid 125 enters vertically oriented outlet 160 and exits cavity 120.

In some embodiments, the sensor comprises a fluid height sensor. Sensors for determining the height of a fluid are generally known in the art and those skilled in the art would be capable of selecting appropriate fluid height sensors based upon the teachings of this specification. In certain embodiments, the sensor comprises a timer. In some such embodiments, the timer may signal the pump to apply a pressure to the fluid internal the cavity at a particular time interval such that the fluid has a particular flow rate through the outlet and/or the fluid has a particular residence time within the cavity such that the product may form. In some embodiments, the pressure is applied to the fluid periodically. Without wishing to be bound by theory, the volume of the first reagent (and/or volumetric flow rate) and the second reagent into the cavity may be determined and the sensor may be configured such that the pump applies a pressure to the fluid internal the cavity when the fluid internal the cavity reaches a particular volume (or height within the cavity).

In some embodiments, the residence time may be selected such that two or more reagents present in the cavity form a product. In some embodiments, the product comprises a plurality of solid particles. In certain embodiments, a fluid may remain in the vessel for a given amount of time (e.g., the residence time). In some cases, the fluid may remain in the vessel for at least about 1 minute, at least about 3 minutes, at least about 5 minutes, at least about 10 minutes, at least about 30 minutes, 1 hour, at least about 2 hours, at least about 4 hours, at least about 8 hours, or at least about 24 hours. In some embodiments, the fluid may remain in the vessel for less than or equal to about 48 hours, less than or equal to 24 hours, less than or equal to about 8 hours, less than or equal to about 4 hours, less than or equal to about 2 hours, less than or equal to about 1 hour, less than or equal to about 30 minutes, less than or equal to about 10 minutes, less than or equal to about 5 minutes, or less than or equal to about 3 minutes. Combinations of the above-referenced ranges are also possible. Other ranges are also possible.

In certain embodiments, the plurality of solid particles are crystallized in the fluid located internal to the cavity from a liquid phase of the fluid. A variety of solvents can be added to the vessel. For example, in some embodiments, the first and/or second reagent is a solvent. Exemplary solvents include, but are not limited to methanol, ethanol, ethyl acetate, butyl acetate, isopropyl acetate, propyl acetate, tert-butyl acetate, sec-butyl acetate, acetone, isopropanol, and/or combinations of these. In certain embodiments, the first and/or second reagent is an antisolvent. The antisolvent can include heptane, isopropyl ether, hexyl acetate, isopentyl acetate, pentyl acetate, toluene, 4-methyl-2-pentanone, isopropanol, and/or combinations of these.

In some embodiments, the vessel comprises a cooling crystallizer. As will be understood by those skilled in the art, a cooling crystallizer generally operates by decreasing the temperature of a fluid such that solid crystals precipitating upon the cooling of the fluid. In some embodiments, the crystallizer comprises an antisolvent crystallization (e.g., an inlet configured to be fluidically connected to an antisolvent). As will be understood by those skilled in the art, antisolvent crystallization generally refers to the use of one or more solvents which reduce the solubility of a solute in the fluid. Other crystallization methods may also be used and will be known in the art. Non-limiting examples of additional crystallization methods and/or crystallizers include reactive crystallization (e.g., wherein the reaction between two or more components of a fluid result in the formation of a solid crystal) melt crystallization (e.g., wherein the fluid comprises two or more solutes which undergoes crystallization at the same or at different temperatures), evaporation crystallization (e.g., wherein by varying temperature to increase the concentration of a solute in a fluid a solid crystal may form), and the like.

For example, in certain embodiments, the vessel may be heated or cooled (e.g., using a heat exchanger, including any of the types of heat exchangers described below, or others). The vessel may be configured to operate, in some cases, at a particular temperature (e.g., a temperature of the fluid within the vessel may be at a particular temperature). For example, the temperature of a fluid in the vessel may range between about 0° C. and about 100° C. In some embodiments, the temperature of a fluid in the vessel may be at least about 0° C., at least about 3° C., at least about 5° C., at least about 10° C., at least about 25° C., or at least about 50° C. In certain embodiments, the temperature of a fluid in the vessel may be less than about 100° C., less than about 50° C., less than about 25° C., less than about 10° C., less than about 5° C., or less than about 3° C. In some embodiments, the temperature within the vessel (e.g., the temperature of the fluid within the cavity of the vessel) is changed during operation. For example, the temperature may change (e.g., increase or decrease) at a rate of greater than or equal to about 0.1° C./min.

In some embodiments, the system comprises a conduit in fluid communication with the vessel, and a valve associated with the conduit switchable from a position releasing pressure from the vessel above a threshold pressure, and to apply pressure internally of the vessel upon a signal indicative of a threshold volume of the product in the vessel. In some embodiments, the systems described herein require relatively low pressures. One of ordinary skill in the art will understand that a valve generally refers to a device which directs and/or controls the flow of a fluid (e.g., by opening or closing a conduit) without fluidically connecting and/or disconnecting a conduit. Non-limiting examples of valves include mechanical valves, ball valves, check valves, butterfly valves, piston valves, pneumatic valves, electronic valves, and hydraulic valves. In some embodiments, the valve comprises two or more ports (e.g., two port valves, three port valves, four port valves, etc.).

Referring again to FIG. 1, in some embodiments, system 100 comprises optional valve 190 fluidically connected to pump 170 and vessel 110, such that undesired pressure may be vented to prevent pressure build up in the vessel as reagents are added to the cavity and/or to facilitate pressure build up during flow of fluid 125.

In some embodiments, the product (e.g., a slurry comprising a plurality of suspended solids) may be transferred to a collection vessel. As shown in FIG. 1, outlet 160 is fluidically connected to collection vessel 180. In some embodiments, pump 170 facilitates the transfer (e.g., upon reaching a critical fluid height or critical residence time) of the product (e.g., fluid 125 comprising a plurality of suspended solids) to collection vessel 180.

Figure 3:
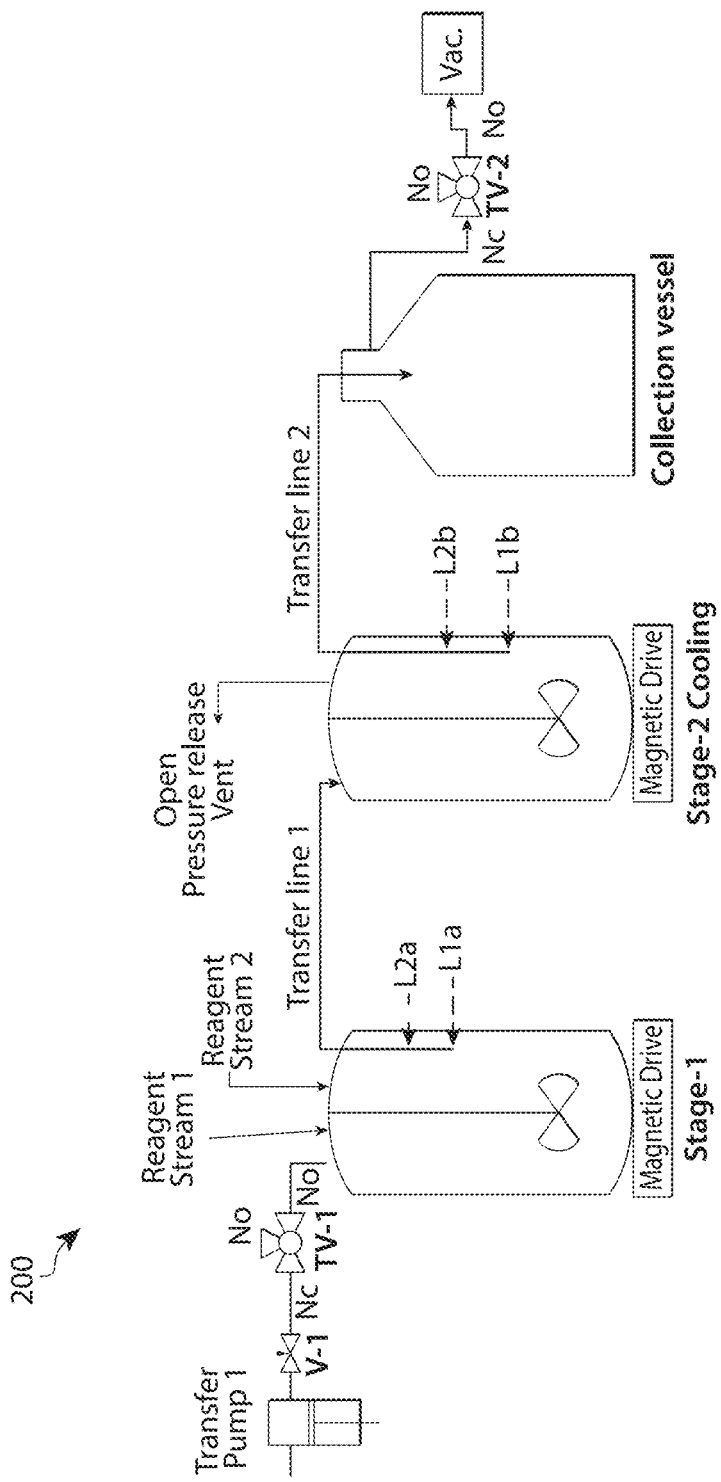
FIG. 3 is a schematic illustration of an exemplary system having two vessels fluidically connected in series, according to some embodiments.

As mentioned above, certain of the systems described herein can be used to produce chemical products. Some embodiments comprise transporting a fluid (e.g., a slurry comprising a plurality of suspended solid particles) through the one or more vessels fluidically connected in series. Some embodiments comprise transporting a first fluid (e.g., a slurry) through a first vessel and a second vessel fluidically connected to the first vessel in series to form a chemical product (which is output from the second vessel). For example, in some embodiments, two or more vessels may be fluidicially connected in series (e.g., each vessel comprising a cavity and a mixing mechanism). For example, as shown in FIG. 3, exemplary system 200 comprises two vessels fluidically connected in series, and a collection vessel.

The various components described herein (e.g., vessel, mixing mechanism, inlets, outlets, pump, valve) may comprise any suitable material (e.g., polypropylene, high density polyethylene, PEEK, PTFE, ETFE, stainless-steel, glass or any other suitable materials).

As noted above, certain of the systems and methods described herein can be used to synthesize an active pharmaceutical ingredient ("API"). In some embodiments, the systems described herein may be used in conjunction with one or more systems for synthesizing an active pharmaceutical ingredient. For example, the systems (e.g., comprising a vessel) described herein may be located downstream of and in fluidic communication with one or more separators, one or more reactors, one or more precipitators, one or more crystallizers, one or more dissolution units, one or more filters, one or more mixers, and/or one or more drying units. For example, in some embodiments, prior to providing to a cavity of a reaction vessel (e.g., through a one or more inlets fluidically connected to the cavity) two or more fluids and mixing the two or more fluids to form a product, one or more of the two or more fluids may be separated, reacted, precipitated, crystallized, filtered, and/or dried. In certain embodiments, one or more filters and/or washing units may be located downstream, and in fluidic communication with, the systems (e.g., comprising a vessel) described herein. For example, in some embodiments, the system may comprise one or more components and/or modules downstream of the vessel including, but not limited to, one or more filters and/or washing units. In some embodiments; the systems and methods described herein may be combined with systems for producing a chemical product as described, for example, in International Patent Application No. WO2016/025803 to Jensen et al. entitled "Systems and Methods for Synthesizing Chemical Products, Including Active Pharmaceutical Ingredients" which is incorporated herein by reference in its entirety for all purposes.

As used herein, the term "active pharmaceutical ingredient" (also referred to as a "drug") refers to an agent that is administered to a subject to treat a disease, disorder, or other clinically recognized condition, or for prophylactic purposes, and has a clinically significant effect on the body of the subject to treat and/or prevent the disease, disorder, or condition. Active pharmaceutical ingredients include, without limitation, agents listed in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange, $8^{th}$ edition (Sep. 21, 2000); Physician's Desk Reference (Thomson Publishing); and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005. Preferably, though not necessarily, the active pharmaceutical ingredient is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as; plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

EXAMPLES

The following examples illustrate embodiments of certain aspects of the invention. It should be understood that the processes described herein may be modified and/or scaled for operation in a large batch or a continuous fashion, as known to those of ordinary skill in the art.

Example 1

The following example describes the use of a pressure-driven flow crystallizer, according to some embodiments described herein.
Single-Stage Mixed Suspension, Mixed Product Removal (MSMPR) Crystallizer.

Feed streams were continuously delivered into the first stage of MSMPR (as shown in FIG. 1) with a diaphragm dosing pump (Model PML-9431-FMM20 manufactured by KNF Flodos AG). The reacting suspension was then transferred out of the MSMPR via a dip tube through the generation of head pressure within the MSMPR vessel. The custom-made crystallizers had a processing scale of between 40 and 200 ml. The feed streams comprised either an API dissolved in solvent which can crystallize in the first stage of the MSMPR due to cooling from the cooling jacket surrounding the crystallizer, or the feed streams consisted of an API solution and an antisolvent stream. The crystallizers used in this study were made of polypropylene and high density polyethylene (HDPE), and had the dimensions of 6×7×7 cm for 40 ml volume and 7.6×9.5×9.5 cm for 200 ml volume. They were stirred to keep solids suspended using a regular magnetic stir bar or a magnetic impeller coated with Teflon (e.g., from HEL Inc.). A dip tube was inserted into the crystallizer and acts as the transfer line to move suspension out of the first stage into the collection vessel or the second stage crystallizer. Adjustment of the dip tube length submerged in the reactor permitted working volumes in a single reactor. A three-way valve (e.g., type 0127 3/2-way Rocker-Solenoid Valve manufactured by Burkert GmbH & Co. KG) was connected to the first stage. The three-way valve (1) allowed the crystallizer to vent thus preventing unwanted pressure build up in the crystallizer as reaction streams were added and (2) facilitated pressure build up during the pressure-driven flow transfer. A solenoid dosing pump to generate pressure within the crystallizer was attached at the normally closed side of the three-way valve.

Figure 2A:
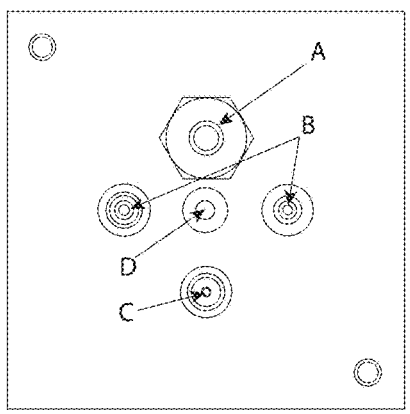
FIGS. 2A-2D are (FIGS. 2A-2C) schematic illustrations and (FIG. 2D) a line drawing of an exemplary pressure driven flow crystallizer (PDFC) with a working volume of 40 mL and with magnetic impeller for both rotational and axial mixing, according to one set of embodiments.
Figure 2C:
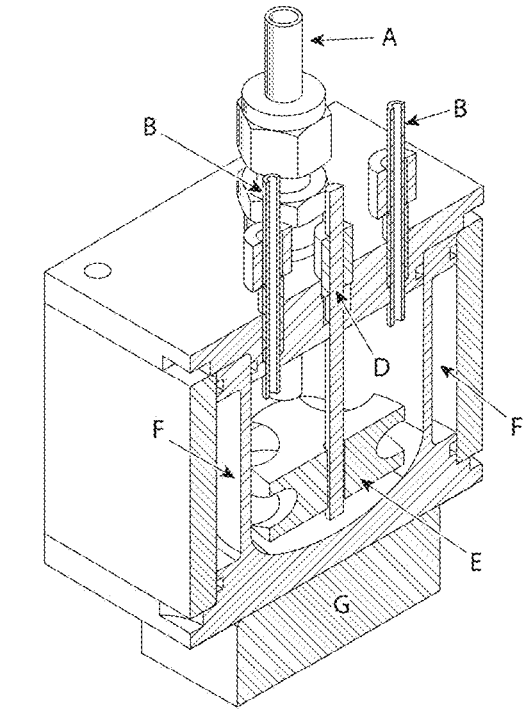
Figure 2B:
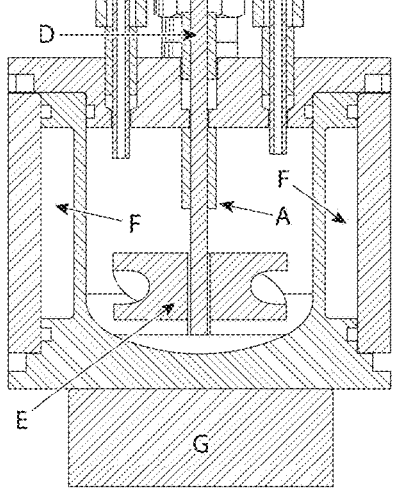
Figure 2D:
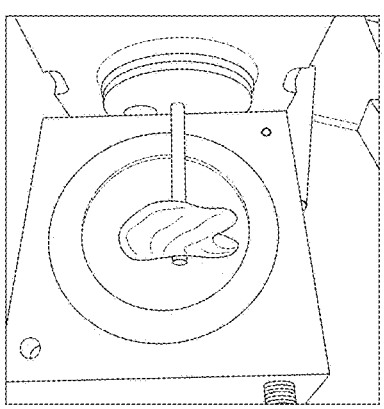

FIGS. 2A-2C are schematics of a custom-made crystallizer with 40 ml working volume. The design is shown from top, side section view and isometric view in perspectives I, II and III respectively with each component labelled. In FIG. 2D, an image is shown of the crystallizer with magnetic PTFE impeller and hastelloy shaft.

Two-Stage MSMPR

In the two-stage MSMPR configuration, the suspension transferred out of Stage 1 is deposited into Stage 2 through Transfer Line 1 (FIG. 3). The vessel for Stage 2 was designed with a Pressure Release Opening, keeping it at ambient pressure so the transfer out of Stage 1 and 2 are independent. Without the pressure relief, transfer of suspension into Stage 2 from Stage 1 could pressurize Stage 2 and cause suspension to be transferred out of Stage 2 through the dip tube (see FIG. 3). The dip tube and Transfer Line 2, installed in Stage 2, transport suspension into the collection vessel when the following two conditions are met: (1) the liquid height exceeds the tip of the dip tube, L1$b$; (2) the normally closed port of the three-way valve, TV-2 (connected to vacuum), is opened, and the normally opened port is closed such that vacuum is applied to the collection vessel which draws suspension out of Stage 2 until its liquid height falls below the dip tube's tip. The withdrawal process was automated with LabView (National Instruments) such that no more than 10% of the total volume is withdrawn for every transfer.

Multi-Stage MSMPR.

Figure 4:
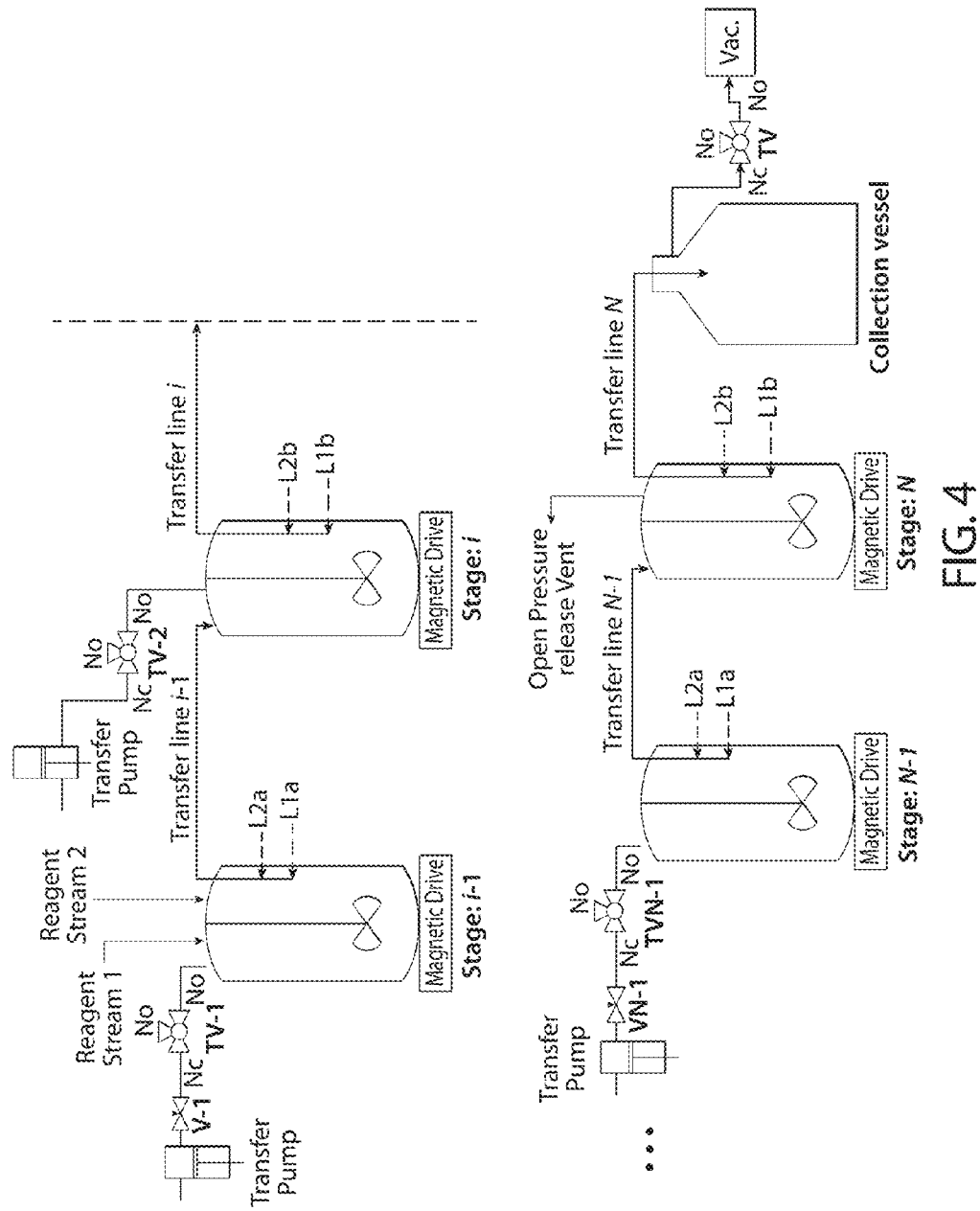
FIG. 4 is a schematic illustration of an exemplary system having N vessels fluidically connected in series, according to some embodiments.

The single- and two-Stage MSMPR systems can be extended to include N crystallization stages. FIG. 4 shows an exemplary arrangement for such a system. In the case of antisolvent crystallization, antisolvent addition ports may be incorporated into each stage in order to increase the driving force for crystallization in stages. Up until stage N, every crystallizer uses a pump to input pressure in order to push suspension out.

The pump and valve operation can be coordinated so that slurry is transferred forward to the next stage. To pump slurry out of stage i, by generating sufficient head pressure therein, the three-way valve of stage i−1 may redirect to close. This can be facilitated by placing a two-way valve at the normally closed side of the three-way (this normally closed side may be opened to connect the flow direction to the crystallizer once the three-way valve is actuated). Setting up the two and three-way valve in this way may prevent the loss of air from stage i−1 when the three way valve is actuated.

In order to transfer slurry out of stage i to stage i+1, the transfer pump and three-way valve connected to stage i may be actuated. This can displace air into stage i, head pressure build up can be lost in stage i through transfer line i−1. In order to prevent further loss of air pressure between stages i and i−1, the three-way valve connected with i−1 (TV1) can be actuated and any pressure loss can be sealed against the two-way valve (V1) which remains closed. This permits the air originally displaced into stage i to build head pressure within stage i and subsequently transfer slurry from stage i to stage i+1 via transfer line i+1 (provided the slurry level is above L1$b$ in stage i). The transfer out from stage i+1 can also proceed by the same mechanism by generating head pressure in the previous two stages, namely, stage i and stage i−1.

The collection vessel following the last stage N can be connected to a vacuum, making the last slurry transfer vacuum-driven as described previously.

Residence Time.

The residence time for stage i can be determined by the following equation:

$$\tau_i = \frac{V_i}{Q_i} \qquad (1)$$

Here, $V_i$ represents the volume of stage i and Q is the volumetric flowrate of the combined reagents going into stage i. The volume of each stage can be controlled by altering the position of the dipping tube and/or installing crystallizers with different total volume. This design allows every stage to be capable of hosting a different working volume, making individual stage residence times flexible. The reactor continues to fill beyond its operating volume, $V_N$, until the three-way valve is opened and the pump turned on. The air (or inert gas) displaced into the reactor pushes the slurry out through the transfer line and returns the liquid height in the reactor to the bottom of the dipping tube. Adding the individual residence times gives the total residence time:

$$\tau = \tau_1 + \tau_2 + \ldots + \tau_{N-1} + \tau_N$$

Example 2

The follow example demonstrates the use of a pressure-driven flow crystallizer, as described in Example 1.

The crystallizers had a working volume of 30 mL. For a feed flow rate of 0.01-10 mL/min, possible residence times can range from 3 min to 50 hour for each stage.

Milliliter-Scale Suspension Handling.

The solubility of azithromycin dihydrate (purchased from Ningbo Samreal Chemical Co. Ltd.) was measured in 60/40 vol % acetone (ACS grade, 99.5% purity purchased from Sigma-Aldrich)/water (18.2 mω resistivity) solvent mixture at various temperatures, and at 20° C. at various antisolvent compositions. At each condition, an azithromycin suspension in the appropriate solvent mixture at the desired temperature was stirred for 48 hours. The suspension was then filtered through a 0.2 μm pore size syringe filter and the mother liquor concentration, i.e. solubility at that condition was measured with High Performance Liquid Chromatography (HPLC, Agilent 1200).

The robustness of the system was demonstrated with a two-stage continuous cooling crystallization of azithromycin in 60/40 vol % acetone/water solvent mixture. A feed solution was prepared with a concentration of 13.6 mg/mL solution. The solution was cooled to 15.0° C. in the first stage, and crystallization was triggered by a combination of cooling and seeding with 50 mg of seed crystals. The second stage was maintained at a temperature of 6.5° C. The residence time (RT) of each stage is 2.0 hours.

Mother liquor concentration in stage 2 was periodically measured by taking a small sample of suspension, filtering it through a syringe filter (0.2 μm) and measuring the concentration with HPLC. In order not to disturb steady state of the entire system, mother liquor concentration of stage 1 was measured from the output of stage 2. Crystal Size Distribution of each stage was also measured with a Focused Beam Reflectance Measurement (FBRM) probe periodically.

The time needed to reach steady state in cooling crystallization described above was compared to that in two-stage antisolvent crystallization. A feed solution of azithromycin dissolved in pure acetone was prepared with a concentration of 28 mg/mL solution. In the first set of experiment, feed solution and antisolvent (water) was pumped into the first stage of MSMPR such that it contained 60 vol % of antisolvent. The content of the first stage crystallizer was transferred through the pressure-driven transfer scheme into the second stage, which additional antisolvent was also pumped into, such that the antisolvent amount was increased to 70 vol % in the second stage. In the second set of experiment, 70 vol % of antisolvent was achieved directly in the first stage of stage, and the content was transferred into the second stage without additional antisolvent. The residence time for both sets of experiment was 15 minutes for each stage, resulting in a total of 30-min residence time. Both stages were maintained at a temperature of 20° C.

Axial Mixing.

FBRM was used in a two-stage MSMPR system to verify whether size classification was taking place. In the first stage, a feed solution of azithromycin dissolved in acetone with a concentration of 20 mg/mL solution was pumped into the first stage of crystallizer with water, resulting in a 70 vol % antisolvent composition. The crystallizer was stirred at 400 rpm by a magnetic axial stirrer, which has a marine propeller coated in Teflon that provides axial mixing in addition to horizontal mixing. A stainless steel shaft goes through the center of the stirrer to confine it to the center of the crystallizer. The suspension was then transferred to the second stage through the dip tube. No antisolvent was added to the second stage, which was also stirred by an axial agitator at 400 rpm. Particle size distribution of both crystallizers was collected by FBRM and compared to each other.

Single-Stage Albuterol Antisolvent Crystallization.

To examine the transfer system's ability to deal with needle-shaped crystals, albuterol hemi sulfate (purchased from Ningbo Samreal Chemical Co. Ltd.) was chosen as the model compound.[19] An albuterol/water solution was prepared with a concentration of 27 mg/mL solution. The solution was pumped into a single stage crystallizer at 0.1 mL/min. The antisolvent, acetone, was pumped into the crystallizer at 1.9 mL/min. The crystallizer was maintained at 20° C. and the residence time was 17.5 min. The previously described transfer scheme was used to intermittently withdraw suspension out of the crystallizer onto a filter paper (0.2 μm pore size) and vacuum filtered. The crystals were then dried in a vacuum oven at 50° C. overnight. Images of the crystals were captured with Nikon optical microscope.

Single-Stage Azithromycin Antisolvent Crystallization.

20 sets of single-stage azithromycin antisolvent crystallization was carried out with the feed solution concentration ranging from 20-40 mg/mL, antisolvent composition ranging 40-70 vol %, and residence time 15-30 min. These experiments were performed to test the possible ranges of particle size and suspension density the system can handle.

Glycine Cooling Crystallization.

Two sets of glycine (ACS grade, 98.5% purchased from Sigma-Aldrich) cooling crystallization were carried out with the feed solution concentration of 267 g/kg water. In one set of the experiment, the first stage was cooled to 22.0° C. and the second to 6.5° C.; in the other, it was a single stage crystallization and the temperature was maintained at 15.0° C. These experiments were carried out to test whether the system can handle large crystals and high suspension densities because glycine crystals grow fast. The suspension density was calculated based on mass balance of feed concentration, mother liquor concentration at steady state, and crystallizer volume described as follows:

$$M_T = \frac{C_{in}Q_{in}\tau - CV}{V}$$

where $M_\tau$ denotes suspension density, $C_{in}$ feed concentration, $Q_{in}$ feed volumetric flow rate, $\tau$ residence time, $C$ mother liquor concentration, and $V$ working volume of the crystallizer.

To test the pressure needed to transfer suspension, a sensitive pressure gauge was connected to the crystallizer. Readings were recorded during transfer of glycine suspension generated from cooling crystallization.

Results

Peristaltic pumps are relatively expensive, and those that can handle organic-solvent-resistant tubing especially so. In this pressure-driven transfer scheme, a diaphragm dosing pump and a short segment of PFA polymer tubing replaced a peristaltic pump. This is cost-effective as the former costs approximately $350 (including one KNF microscale dosing pump and 6 in. ⅛" OD PFA polymer tubing), while the latter's retail price is approximately $2,330. Furthermore, PFA tubing is resistant to a wider range of organic solvents than the precision tubing typically required by the peristaltic pump heads, which affords extra flexibility.

The total footprint of a two-stage MSMPR system with pressure-driven transfer scheme is only 4,800 cm³, including the two crystallizers each with 40-mL maximum volume, valves and pumps. In comparison, the volume of a single Masterflex peristaltic pump (Cole-Parmer, Masterflex L/S Digital Drive 600 RPM) is 7,360 cm³. With such a small footprint, the system is flexible to accommodate more stages within limited space. Reduced pump size coupled with automation more easily facilitates a modular processing scheme where a number of crystallizer stages can be added or removed on demand.

Figure 5:
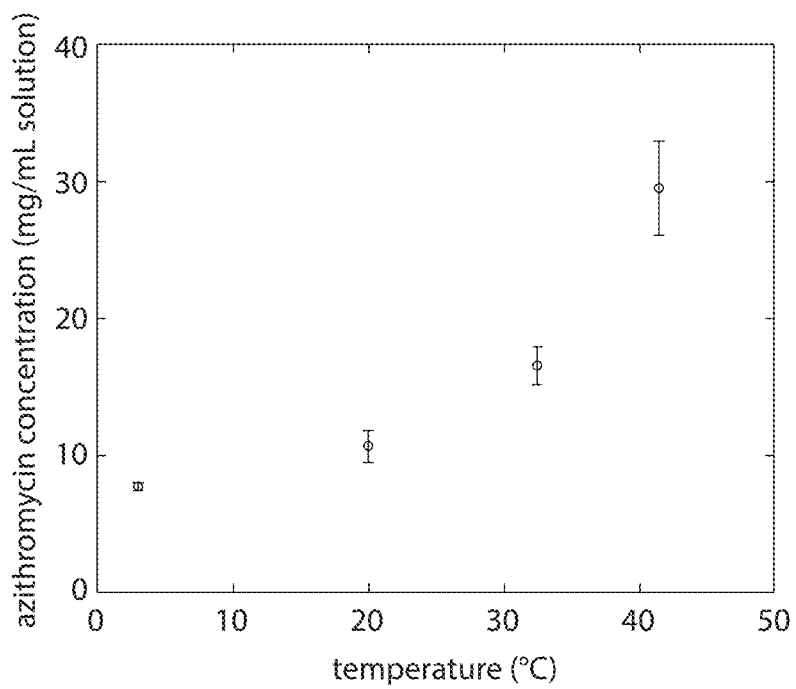
FIG. 5 is a plot of Azithromycin solubility in 40 vol % antisolvent as a function of temperature, according to one set of embodiments.
Figure 6:
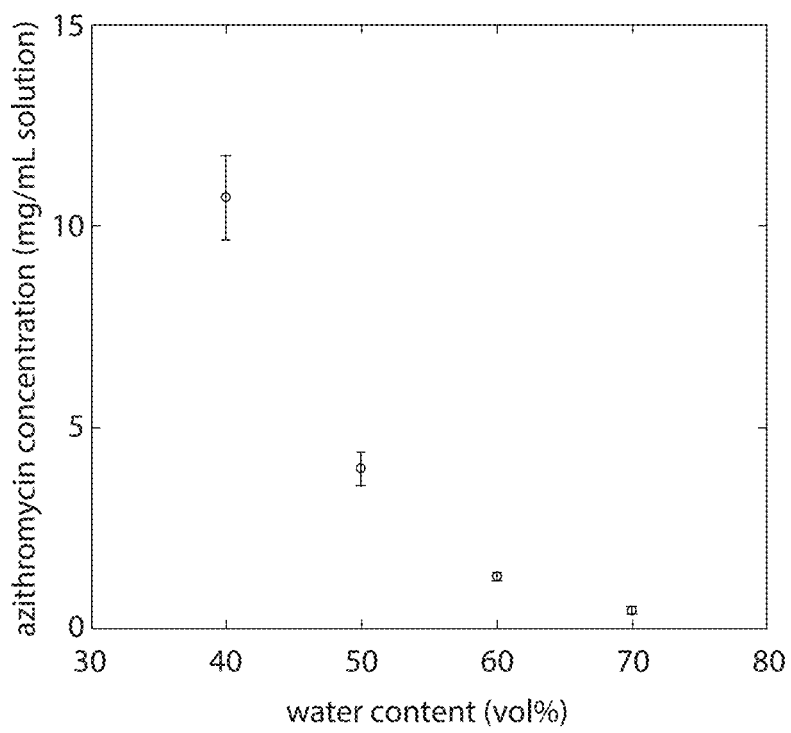
FIG. 6 is a plot of Azithromycin solubility at various antisolvent compositions at 20° C., according to one set of embodiments.

FIG. 5 shows the solubility of azithromycin in a 60/40 vol acetone/water solvent mixture at various temperatures. FIG. 6 shows the solubility of azithromycin as a function of antisolvent composition at 20° C.

Figure 7A:
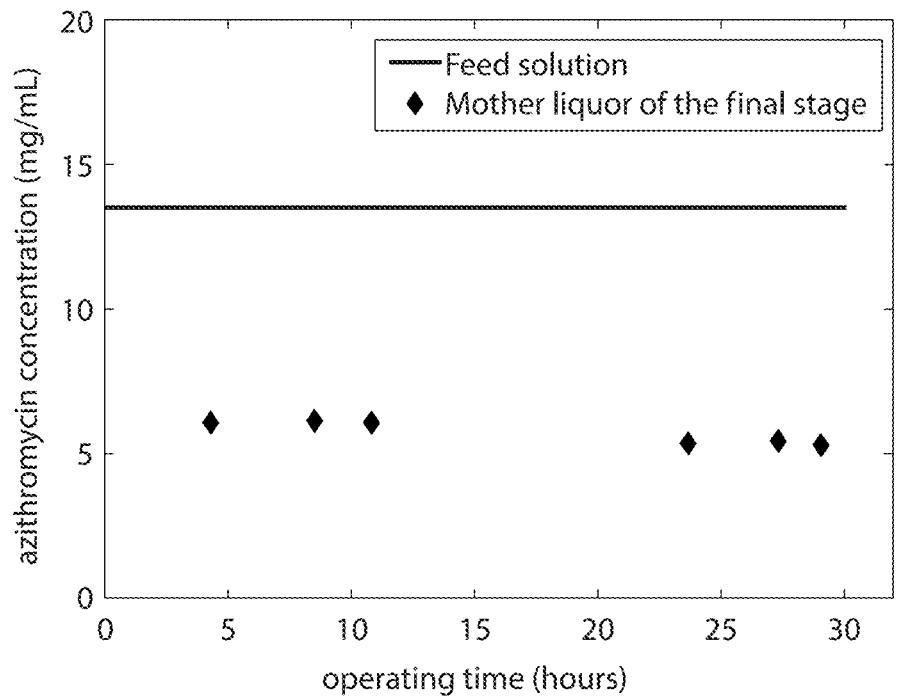
FIG. 7A is a plot of Azithromycin concentration of the mother liquor of the final stage of the system compared to that of the feed solution during the two-stage continuous cooling crystallization of azithromycin in 60/40 vol % acetone/water solvent mixture.
Figure 7B:
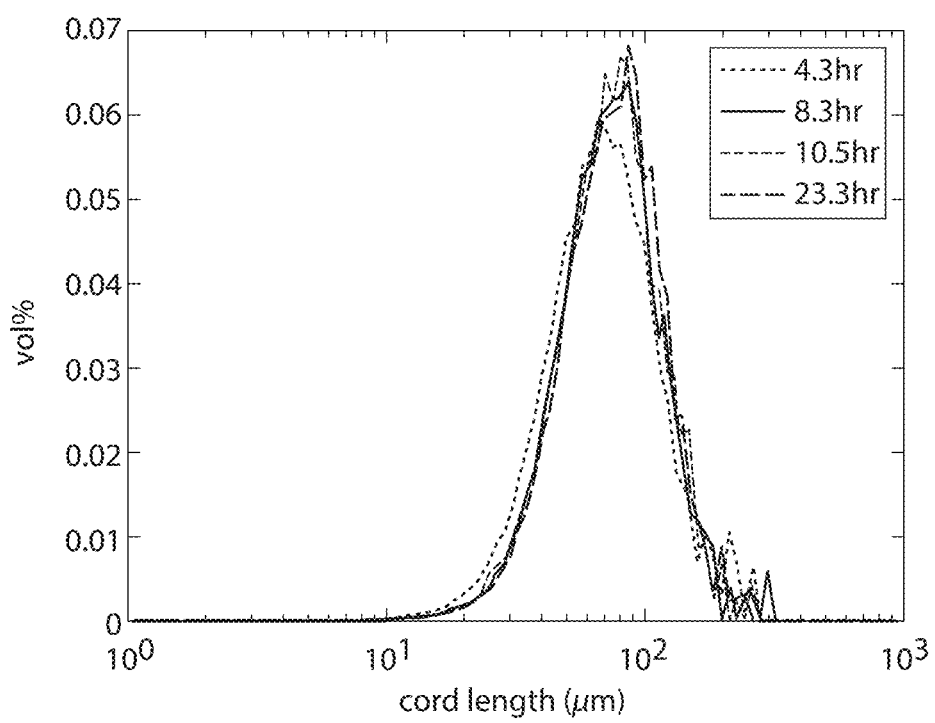
FIG. 7B is a plot of time-evolvement of particle size distribution of the final stage of the system.

During the two-stage continuous cooling crystallization of azithromycin in 60/40 vol % acetone/water solvent mixture, steady state was monitored by mother liquor concentration as well as the particle size distribution of the final stage of MSMPR, as shown in FIG. 7A-7B. FIGS. 7A-7B show that the automated system can operate robustly for more than 24 hours. Furthermore, the temporal behavior of mother liquor concentration and crystal size distribution shows steady state can be reached in this system within two residence times (RT).

Figure 8:
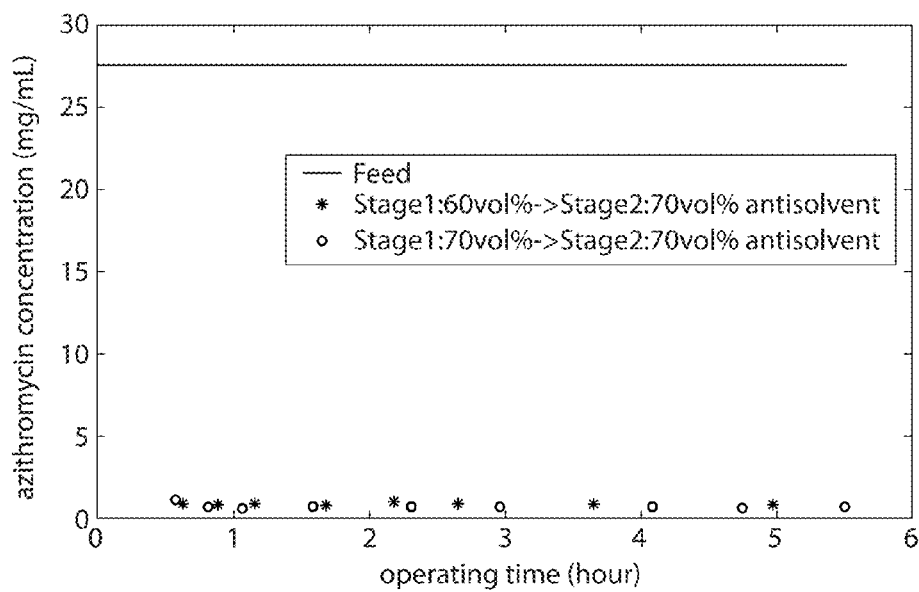
FIG. 8 is a plot of Azithromycin concentration in the second stage of the system in two sets of two-stage antisolvent crystallization compared to that of the feed solution.

It was observed that the system reaches steady state fast in two-stage antisolvent crystallization. In both antisolvent crystallization experiments, the mother liquor concentration of azithromycin was monitored throughout the operation as shown in FIG. 8. It can be seen FIG. 8 that steady state was reached within two RTs for both sets of experiment. Furthermore, the feed solution was almost completely desupersaturated, resulting in a 98% yield. These two sets of experiment, however, generated different particle size distribution in the final product, as shown in FIG. 9.

Figure 9:
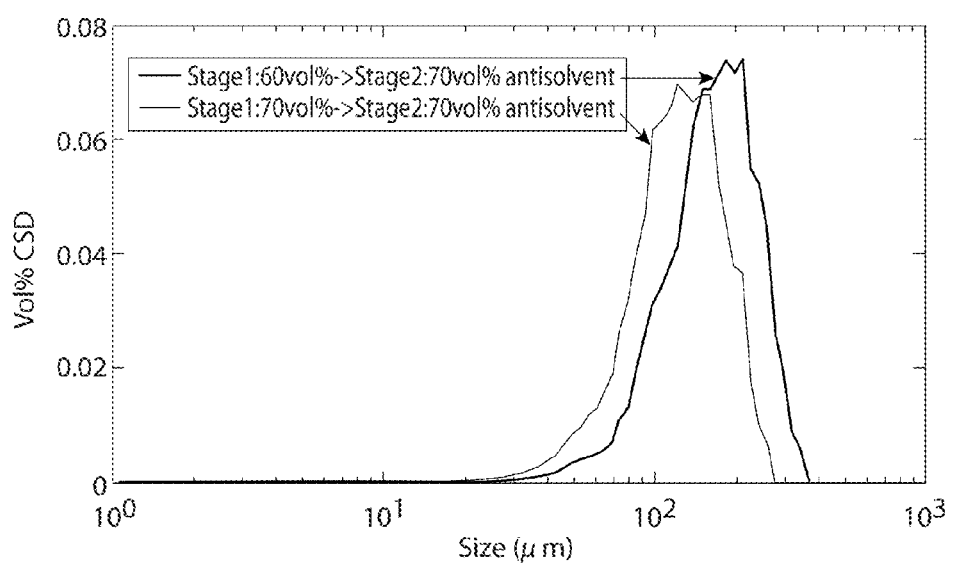
FIG. 9 is a plot of two exemplary sets of antisolvent crystallization schemes with the same residence time generated different particle size distribution.

FIG. 9 shows different particle size distribution can be obtained by splitting the addition of antisolvent. APIs often have different nucleation and growth rate under different antisolvent composition. The multi-stage MSMPR system takes advantage of such features, and can generate crystals of different sizes.

Transfer schemes involving dip tubes often invites concerns on size classification of particles. Indeed, to attain isokinetic withdrawal of suspension, there generally needs to be effective mixing to sustain a homogeneous suspension of solids in the crystallizer. If the suspension in the first stage is well mixed and homogenous, the second stage may have comparable numbers of crystals with slightly larger particle size. On the contrary, when crystal size classification takes place, the second stage may have fewer and smaller crystals compared to the first stage since only the fines on the top are expected to be withdrawn. A comparison of particle size distribution in two stages of MSMPR with axial mixer is shown in FIG. 10.

Figure 10:
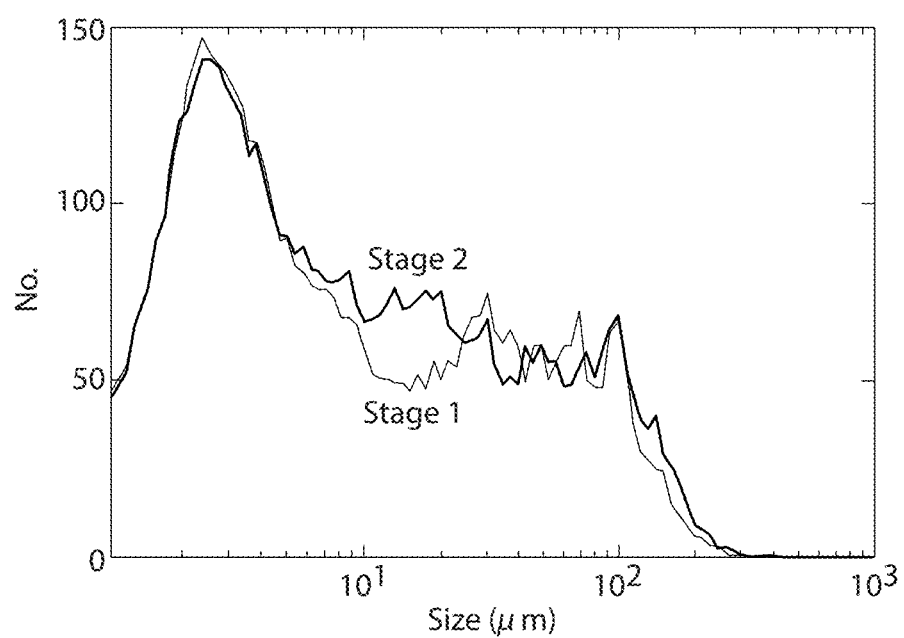
FIG. 10 is a plot comparing particle size distribution in two stages of the system with mixing provided by an axial agitator.

FIG. 10 shows the second stage had comparable numbers of crystals as the first stage with slightly larger particle size, indicating sufficient mixing and no crystal size classification.

The pressure driven transfer system is flexible in many aspects. Besides the flexibility to perform cooling and/or antisolvent crystallization, accommodate a variety of solvents (anything compatible with polypropylene, HDPE and PFA), and achieve a large range of residence time, the system can also handle crystals of different shapes. Crystals with large and small aspect ratios (FIGS. 11A-11B) were tested and could be successfully transferred between crystallizers.

The system can also handle a wide range of particle sizes and suspension density. The median crystal cord length tested in the system ranged from 58 to 194 μm. The smallest and largest crystal sizes were plotted in FIG. 12. The slurry density ranged from 0.7 to 87 mg/mL.

The pressure needed to transfer a glycine water suspension (87 mg/mL) was measured to be 10 inch water gauge, or 0.36 psig (transfer height ~4 in.). This pressure is relatively small and was generally sufficient for transferring on a small scale as demonstrated in this study. For understanding the transfer of slurry on other scales, the pressure required for transfer can be roughly estimated from the Bernoulli equation modified to account for frictional losses. For a suspension with density p, the governing equation from the starting point of the dip tube (point 0) to the highest point of the dip tube (point 1) is $$h_0 + \frac{P_0}{\rho g} + \frac{v_0^2}{2g} + \Delta h_p = h_1 + \frac{P_1}{\rho g} + \frac{v_1^2}{2g} + \Delta h_f + \Delta h_m$$

where h denotes height, P pressure, v fluid velocity, $\Delta h_p$ pump input (zero in this case), $\Delta h_f$ frictional loss, $\Delta h_m$ loss due to entrance/exit/fitting, and g gravitational constant. Assume laminar flow in a circular pipe, that the velocities at both point 0 and 1 are zero, and that point 1 is at ambient pressure, the design equation for estimating pressure needed to transfer a suspension can be reduced to $$P = P_{atm} + \rho g \left( \Delta h + \frac{128 \mu L Q}{\pi \rho D^4 g} + \frac{8 \Sigma K Q^2}{g \pi^2 D^2} \right)$$

where $P_{atm}$ is the atmospheric pressure, μ is the viscosity of solvent, L is tube length, Q is volumetric flow rate, D is inner tube diameter, K is constant for entrance/exit/fitting losses. This equation assumes the velocity of the suspension is zero before and after the transfer, and thus is the minimum pressure needed.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method comprising:
providing a reaction vessel including at least one inlet for introduction of a reactant, and at least one outlet for recovery of a product, wherein the outlet is constructed and arranged such that it facilitates removal of the product when a volume of substance in the vessel is at least a threshold volume, but not to facilitate removal of the product when a volume of substance in the vessel is below the threshold volume; and
controlling pressure internally of the vessel so as to remove a given volume of the product from the vessel when the volume of substance in the vessel is at least at the threshold volume, while not removing a volume of the product from the vessel when the volume of substance in the vessel is below the threshold volume.

2. A method as in claim 1, further comprising:
controlling pressure internally of the vessel to release, from the vessel, pressure above a threshold pressure when the volume of substance in the vessel is below the threshold volume.

3. A system comprising:
a reaction vessel including at least one inlet for introduction of a reactant, and at least one outlet for recovery of a product;
a sensor constructed to determine volume of the product in the vessel; and
a conduit in fluid communication with the vessel, and a valve associated with the conduit switchable from a position releasing pressure from the vessel above a threshold pressure, and to apply pressure internally of the vessel upon a signal indicative of a threshold volume of the product in the vessel.

4. A method for crystallizing a compound, comprising:
providing to a cavity of a reaction vessel, through a first inlet fluidically connected to the cavity, a first fluid;
providing to the cavity of the reaction vessel, through a second inlet fluidically connected to the cavity, a second fluid;
mixing the first fluid and the second fluid to form a product;
measuring the volume of the product in the cavity; and
upon reaching a critical vertical volume of the product, applying a pressure to the cavity such that at least a portion of the product flows through a vertically oriented outlet fluidically connected with the cavity to a receiving vessel,
wherein the cavity has a volume of less than 1 L and/or wherein a flow rate of the fluid through the vertically oriented outlet is greater than a sedimentation rate of the product in the fluid.

5. A method as in claim 4, wherein the receiving vessel is a second reaction vessel.

6. A method for crystallizing a compound, comprising:
providing to a cavity of a reaction vessel, through a first inlet fluidically connected to the cavity, a first fluid;
providing to the cavity of the mixing vessel, through a second inlet fluidically connected to the cavity, a second fluid;
mixing the first fluid and the second fluid to form a product; and
periodically applying a pressure to the cavity such that at least a portion of the product flows through a vertically oriented outlet fluidically connected with the cavity to a receiving vessel, wherein the cavity has a volume of less than 1 L and/or wherein a flow rate of the fluid through the vertically oriented outlet is greater than a sedimentation rate of the product in the fluid.

7. A system, comprising:
a vessel comprising a mixing mechanism and a cavity;
a first inlet fluidically connected to the cavity;
a second inlet fluidically connected to the cavity;
a vertically oriented outlet fluidicially connected to the cavity; and
a pump, configured to apply a pressure to the cavity periodically, wherein
the volume of the cavity is less than 1 L.

8. A system, comprising:
a vessel comprising a mixing mechanism and a cavity;
a first inlet fluidically connected to the cavity;
a second inlet fluidically connected to the cavity;
a vertically oriented outlet fluidicially connected to the cavity;
a fluid height sensor; and
a pump, configured to apply a pressure to the cavity upon a fluid internal to the cavity reaches a critical fluid height, wherein the volume of the cavity is less than 1 L.

9. A method as in claim 4, wherein the first fluid comprises a crystallizable compound.

10. A method as in claim 4, wherein the second fluid comprises an antisolvent.

11. A method as in claim 4, wherein the volume of the cavity is less than 100 mL.

12. A method as in claim 1, wherein the vessel comprises an antisolvent crystallizer.

13. A method as in claim 1, wherein the temperature within the vessel is changed during operation.

14. A system as in claim 3, wherein the reaction vessel is a first reaction vessel and comprising one or more additional reaction vessels fluidically connected in series with the first reaction vessel.

15. A system as in claim 7, wherein the vessel is a first vessel and comprising one or more additional vessels fluidically connected in series with the first reaction vessel.

16. A method as in claim 1, wherein the product is a fluid comprising a plurality of suspended solids.

17. A method as in claim 4, wherein the flow rate of the fluid is less than 10 milliliters per minute.

18. A method as in claim 1, wherein the product is an active pharmaceutical ingredient.

* * * * *